US009072631B2

(12) United States Patent
Nakajima et al.

(10) Patent No.: US 9,072,631 B2
(45) Date of Patent: Jul. 7, 2015

(54) ABSORBENT ARTICLE WITH LEAKING-PREVENTION UNITS HAVING ELASTIC MEMBERS

(75) Inventors: Osamu Nakajima, Kanonji (JP); Yuichi Suzuki, Kanonji (JP); Yuki Noda, Kanonji (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 642 days.

(21) Appl. No.: 13/321,423

(22) PCT Filed: May 17, 2010

(86) PCT No.: PCT/JP2010/058260
§ 371 (c)(1),
(2), (4) Date: Jan. 19, 2012

(87) PCT Pub. No.: WO2010/134480
PCT Pub. Date: Nov. 25, 2010

(65) Prior Publication Data
US 2012/0116344 A1    May 10, 2012

(30) Foreign Application Priority Data

May 18, 2009    (JP) .................................. 2009-119572

(51) Int. Cl.
*A61F 13/15*    (2006.01)
*A61F 13/20*    (2006.01)
(Continued)

(52) U.S. Cl.
CPC ....... *A61F 13/4753* (2013.01); *A61F 13/15723* (2013.01); *A61F 13/15739* (2013.01);
(Continued)

(58) Field of Classification Search
CPC .............. A61F 13/475; A61F 13/4751; A61F 13/4752; A61F 13/4756; A61F 13/4757; A61F 13/494; A61F 13/4753; A61F 13/49011; A61F 13/49014; A61F 13/49019; A61F 13/4902; A61F 13/4942
USPC ............................................. 604/380, 385.27
See application file for complete search history.

(56) References Cited

U.S. PATENT DOCUMENTS 5,080,658 A * 1/1992 Igaue et al. ............... 604/385.27
5,810,800 A   9/1998 Hunter et al.
(Continued)

FOREIGN PATENT DOCUMENTS

EP    0 998 893    5/2000
JP    6-254119    9/1994
(Continued)

OTHER PUBLICATIONS

Extended European Search Report dated May 17, 2013, directed to EP Application No. 10777713.8; 6 pages.
(Continued)

*Primary Examiner* — Michele M Kidwell
(74) *Attorney, Agent, or Firm* — Morrison & Foerster LLP (57) ABSTRACT

A leakage-preventing unit 50 of an absorbent article 1 is formed by elastic members 51 and sheets 52. The leakage-preventing unit 50 includes a central region C and a pair of end unit regions S positioned outside a longitudinal direction L from the central region C.
The elastic members 51 includes
a fixed unit 51A fixed to the sheet 52 in a state when the elastic members 51 extend in the longitudinal direction L and a free end 51B positioned outside the longitudinal direction L from the fixed unit 51A, which is not fixed to the sheet 52. The end unit regions S includes a joint processing unit 53A in which a joint process for joining the portions where the sheets 52 face each other is performed and a non-joint processing unit 53B in which the joint process is not performed. The free end 51B is arranged in the non-joint processing unit 53B.

4 Claims, 10 Drawing Sheets

(51) Int. Cl.
  *A61F 13/475* (2006.01)
  *A61F 13/472* (2006.01)
  *A61F 13/515* (2006.01)
  *A61F 13/494* (2006.01)

(52) U.S. Cl.
  CPC ..... *A61F13/15756* (2013.01); *A61F 13/47263* (2013.01); *A61F 13/515* (2013.01); *A61F 13/4942* (2013.01)

(56) References Cited

U.S. PATENT DOCUMENTS

| | | |
|---|---|---|
| 6,248,097 B1 | 6/2001 | Beitz et al. |
| 7,641,642 B2 | 1/2010 | Murai et al. |
| 7,794,441 B2 * | 9/2010 | Ashton et al. ............ 604/385.28 |
| 2002/0138060 A1 | 9/2002 | Nabaoka et al. |
| 2010/0191209 A1 | 7/2010 | Nomoto et al. |

FOREIGN PATENT DOCUMENTS

| | | |
|---|---|---|
| JP | 2000-342623 | 12/2000 |
| JP | 2002-522117 | 7/2002 |
| JP | 2003-245306 | 9/2003 |
| JP | 2008-142315 | 6/2008 |
| JP | 2009-6065 | 1/2009 |
| WO | WO-94/18927 | 9/1994 |
| WO | WO-96/23471 | 8/1996 |
| WO | WO-00/66351 | 11/2000 |

OTHER PUBLICATIONS

Office Action dated Sep. 12, 2013, directed to Mexican Application No. MX/A/2011/012322; 7 pages.
Notification on need to provide additional documents dated Oct. 28, 2013, directed to Eurasian Application No. 201101642; 3 pages.
Office Action dated Sep. 10, 2013, directed to CA Application No. 2,762,666; 3 pages.
Context of First Official Notice of Reasons for Rejection dated Jul. 3, 2013, directed to Chinese Patent Application No. 201080022158.9; 8 pages.
International Search Report mailed Aug. 24, 2010, directed to International Patent Application No. PCT/JP2010/058260; 5 pages.
Technical Report dated Jul. 1, 2014, directed to EG Application No. 2011111958; 10 pages.
Office Action dated Feb. 17, 2014, directed to EP Application No. 10 777 713.8; 3 pages.

* cited by examiner

ABSORBENT ARTICLE WITH LEAKING-PREVENTION UNITS HAVING ELASTIC MEMBERS

REFERENCE TO RELATED APPLICATIONS

This application is a national stage application under 35 USC 371 of International Application No. PCT/JP2010/058260, filed May 17, 2010, which claims the priority of Japanese Application No. JP2009-119572, filed May 18, 2009, the contents of which prior applications are incorporated herein by reference.

FIELD OF THE INVENTION

The present invention relates to an absorbent article in which a pair of leakage-preventing units are provided along a longitudinal direction of the absorbent article on both side units in a widthwise direction of the absorbent article.

BACKGROUND OF THE INVENTION

Conventionally, on both side units of a topsheet side in a widthwise direction of an absorbent article, such as a sanitary napkin, a pair of leakage-preventing units (so-called solid gathers) that expand and contract along a longitudinal direction of the absorbent article are provided. Generally, the leakage-preventing units are configured by elongated elastic members (for example, rubber) that expand and contract in the longitudinal direction of the absorbent article, and a nonwoven fabric (sheet) that wraps the elastic members along the longitudinal direction of the absorbent article.

Such a leakage-preventing unit includes a central region in the longitudinal direction of the absorbent article, and a pair of end unit regions positioned outside the longitudinal direction of the absorbent article from the central region. In the outer end of the longitudinal direction of the absorbent article in the end unit region, the elastic members are fixed to the nonwoven fabric in an extended state in the longitudinal direction of the absorbent article. Therefore, at the time of wearing, due to shrinkage of the elastic members, the leakage-preventing units rise toward the wearer from both side units of the absorbent article (For example, see Patent Document 1).

However, in the aforementioned conventional absorbent article, because the elastic members were extended between the outer ends in a pair of end unit regions, there was a problem of deformation of the form of the absorbent article at the time of wearing as the end unit regions would fall easily in the central region (absorbing surface) side by more than needed, at the time of wearing, due to shrinkage of the elastic members along the longitudinal direction of the absorbent article.

In order to prevent this, it is considered that the form of the absorbent article can be stabilized by joining the end unit regions to form one part with the absorber, whose flexural rigidity is more than that of the leakage-preventing units. In such a case, because it is necessary to secure as large an area as possible, that is, to increase the area in which the absorber and the end unit regions are joined, along the longitudinal direction of the absorbent article, the flexibility of the end unit regions where the joint process was executed is lost. Thus, at the time of wearing, when the end unit regions contact the wearer, there arises a new problem that the wearer's comfortable feel against the skin from is worsened.

RELATED ART DOCUMENT

[Patent Document 1] Japanese Unexamined Patent Application Publication No. 2003-245306 (Page 2 to 3, FIG. 8 and FIG. 10)

SUMMARY OF INVENTION

An absorbent article according to the first feature includes a topsheet having liquid permeability, a backsheet having liquid impermeability, an absorber provided between the topsheet and the backsheet, and a pair of leakage-preventing units provided on both side units in the widthwise direction of the absorbent article with a leakage-preventing unit being configured by elastic members arranged along the longitudinal direction of the absorbent article, and sheets arranged along the longitudinal direction, which wrap the elastic members and have at least a part fixed to the topsheet, wherein the leakage-preventing unit includes: central region (central region C) in the longitudinal direction; and a pair of end unit regions (end unit region 5) positioned outside the longitudinal direction from the central region, the elastic members comprise: a fixed unit (fixed unit 51A) fixed to the sheet in a state when the elastic members extend in the longitudinal direction in at least the boundary of the central region and the end unit regions; and a free end (free end 51B) positioned outside the longitudinal direction from the fixed unit, which is not fixed to the sheet, the end unit regions includes a joint processing unit (joint processing unit 53A) in which a joint process for joining the portions where the sheets face each other is performed; and a non-joint processing unit (non-joint processing unit 53B) in which the joint process is not performed, and the free end is arranged in the non-joint processing unit.

BRIEF DESCRIPTION OF DRAWINGS

FIG. 3 (a) is an enlarged plan view showing a part of a leakage-preventing unit 50 according to the present embodiment, and FIG. 3 (b) is an enlarged plan view showing a part of a joint processing unit 53A according to the present embodiment.

DETAILED DESCRIPTION OF THE INVENTION

Hereinafter, an absorbent article according to an embodiment is described with reference to drawings. In the following description of the drawings, the same or similar reference numerals are used to designate the same or similar parts. It will be appreciated that the drawings are schematically shown and the ratio and the like of each dimension are different from the real ones. Therefore, detailed dimension and the like should be determined considering the following description. Of course, among the drawings, the dimensional relationship and the ratio are different.

Figure 1:
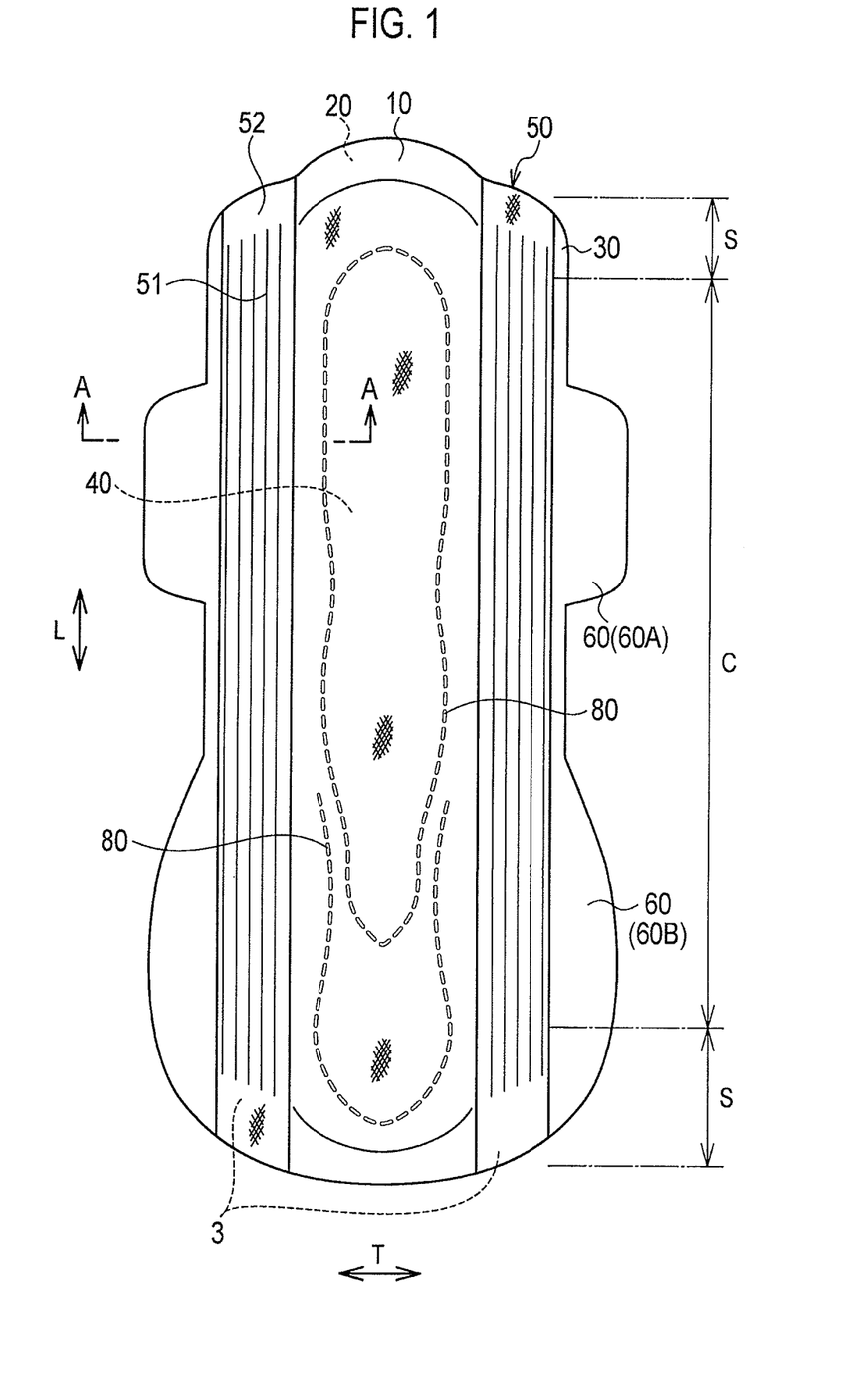
FIG. 1 is a plan view showing an absorbent article 1 according to the present embodiment.
Figure 2:
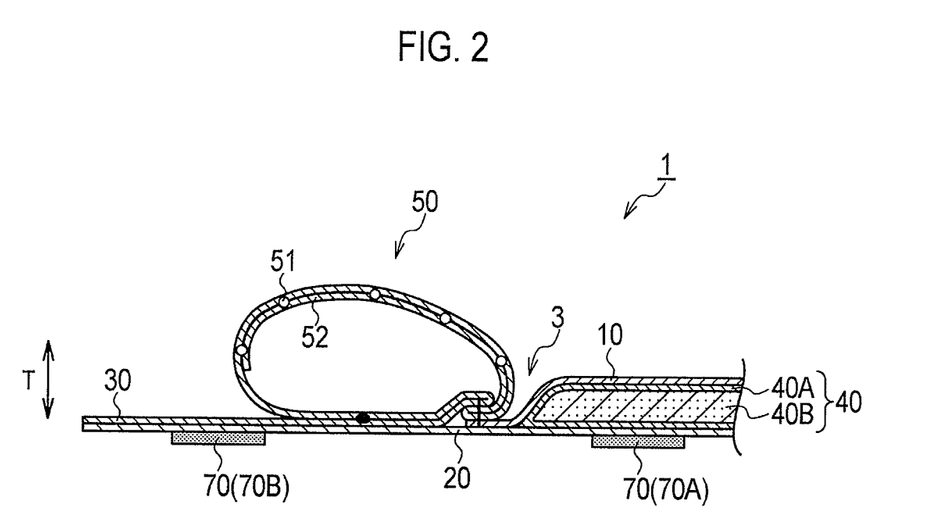
FIG. 2 is a cross-sectional view of a part (cross-sectional view of A-A of FIG. 1) of the absorbent article 1 according to the present embodiment.

First of all, a configuration of an absorbent article 1 according to the present embodiment is explained with reference to drawings. FIG. 1 is a plan view showing the absorbent article 1 according to the present embodiment. FIG. 2 is a cross-sectional view of a part (cross-sectional view of A-A of FIG. 1) of the absorbent article 1 according to the present embodiment. Note that in the present embodiment, the absorbent article 1 is a sanitary napkin.

As shown in FIG. 1 and FIG. 2, the absorbent article 1 has a longitudinally elongated shape toward the front-back direction (hereinafter, the longitudinal direction L of the absorbent article 1) corresponding to the direction facing the backside (literally, "back" side) from the foreside (stomach side) of the wearer.

The absorbent article 1 includes a topsheet 10, a backsheet 20, a sidesheet 30, an absorber 40, and leakage-preventing units 50. Furthermore, a wing unit 60, an adhesive unit 70, and a joint unit 80 are formed in the absorbent article 1.

The topsheet 10 is provided on the side that is in contact with the skin of the wearer. The topsheet 10 is formed by a liquid-permeable sheet such as an air-through nonwoven fabric (for example, polyethylene terephthalate and polyethylene).

The backsheet 20 is provided on the side that is in contact with the shorts. The backsheet 20 is formed by a liquid-impermeable sheet such as a water-resistive film (for example, polyethylene).

The sidesheet 30 is provided outside the widthwise direction W perpendicular to the longitudinal direction L of the absorbent article 1 with respect to the topsheet 10. The sidesheet 30 is formed by a liquid-permeable sheet such as a spunbond nonwoven fabric (for example, polypropylene and polyethylene).

The absorber 40 is provided between the topsheet 10 and the backsheet 20, and has a longitudinally elongated shape similar to the absorbent article 1. The absorber 40 is formed by an absorbent material 40A that absorbs the bodily waste of the wearer, and a covering material 40B that covers the absorbent material 40A. The absorbent material 40A includes a mixed powder of ground pulp and high absorbent polymer. The covering material 40B includes a tissue.

Here, in the present embodiment, the aforementioned topsheet 10, backsheet 20, sidesheet 30, and absorber 40 are each joined by an adhesive (for example, hot melt) and thermal fusion bonding.

The leakage-preventing units 50 are provided on both side units 3 in the widthwise direction W of the absorbent article 1. The leakage-preventing unit 50 is described later.

The wing unit 60 is formed toward the outer side of the widthwise direction W of the absorbent article 1 by extending the backsheet 20 and the sidesheet 30 farther than the absorber 40. The wing unit 60 is configured by an anterior wing unit 60A folded back in the crotch unit of the shorts, and a posterior wing unit 60B provided at the backside of the wearer from the anterior wing unit 60A and extending outside the widthwise direction W of the absorbent article 1 along the shape of the shorts.

The adhesive unit 70 is formed by a member (for example, hot melt) having adhesiveness that enables it to be fixed to the shorts. The adhesive unit 70 is provided on a surface at the opposite side of the surface where the absorber 40 of the backsheet 20 is provided.

Specifically, the adhesive unit 70 possesses a long adhesive unit 70A and a short adhesive unit 70B. The long adhesive unit 70A extends along the longitudinal direction L of the absorbent article 1. The short adhesive unit 70B is shorter than the long adhesive unit 70A and is provided in the portion that configures the wing unit 60 of the backsheet 20.

The joint unit 80 is formed by adding pressure to at least the topsheet 10 and the absorber 40 (for example, by subjecting the same to embossing) in the thickness direction T of the absorbent article 1 so as to join at least the topsheet 10 and the absorber 40.

Figure 3:
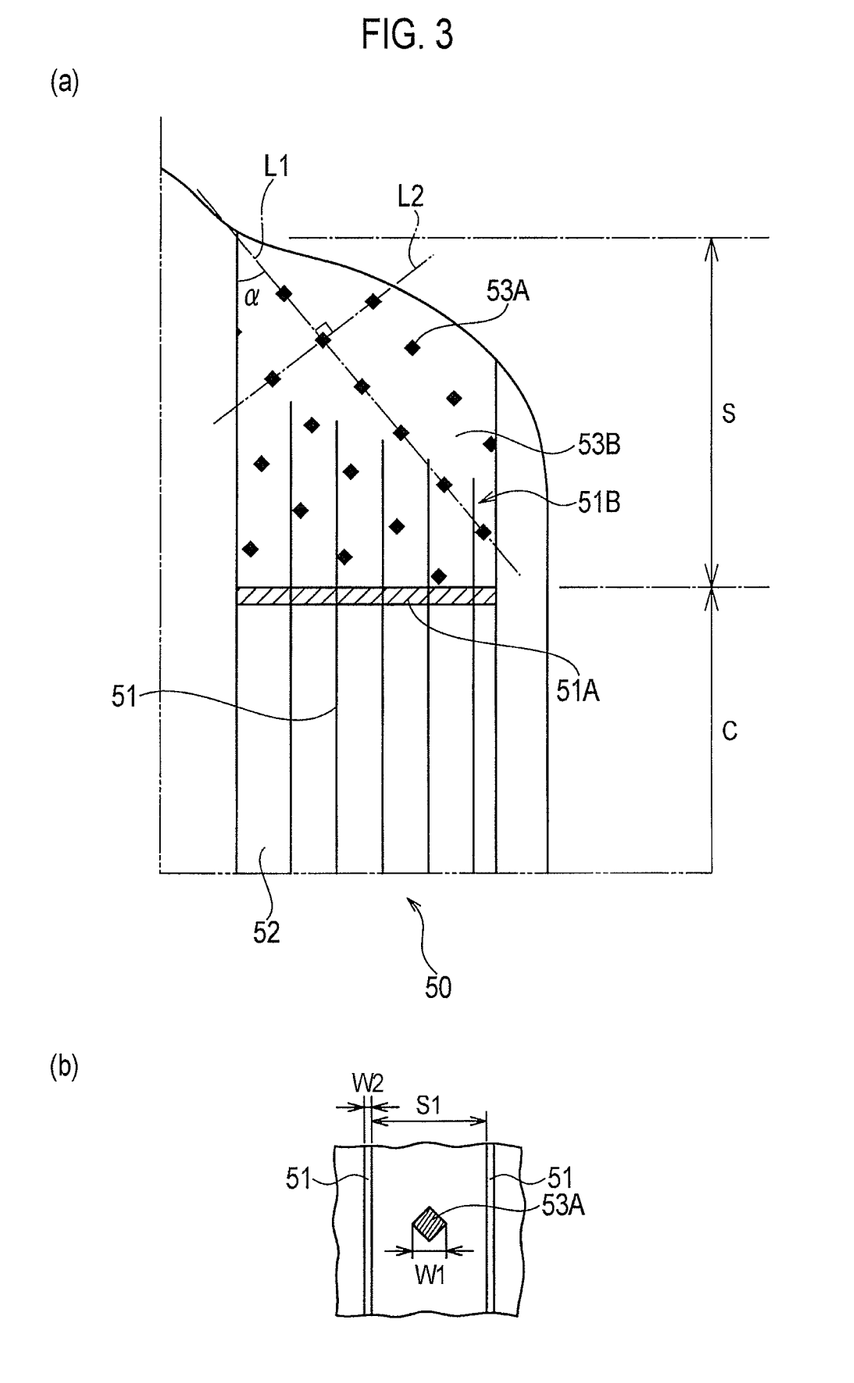

Next, the configuration of the leakage-preventing unit 50 according to the present embodiment is explained with reference to FIG. 1 through FIG. 3. FIG. 3 (a) is an enlarged plan view showing a part of the leakage-preventing unit 50 according to the present embodiment. FIG. 3 (b) is an enlarged plan view showing a part of the joint processing unit 53A according to the present embodiment.

As shown in FIG. 1 through FIG. 3, the leakage-preventing unit 50 has a central region C in the longitudinal direction L of the absorbent article 1, and a pair of end unit regions S positioned outside the longitudinal direction L of the absorbent article 1 from the central region C. Furthermore, the leakage-preventing unit 50 is configured by elastic members 51 and sheets 52.

The elastic members 51 are arranged along the longitudinal direction L of the absorbent article 1. A plurality (five in the present embodiment) of elastic members 51 are provided at a predetermined interval in the widthwise direction W of the absorbent article 1. An elastic member 51 has a fixed unit 51A and a free end 51B.

The fixed unit 51A is fixed to a sheet 52 in a state where the elastic members 51 extend in the longitudinal direction L of the absorbent article 1 in at least the boundary of the central region C and the end unit regions S. The free end 51B is positioned outside the longitudinal direction L of the absorbent article 1 from the fixed unit 51A and is not fixed to the sheet 52. The free end 51B is arranged in the non-joint processing unit 53B described later.

The sheets 52 are arranged along the longitudinal direction L of the absorbent article 1. The sheets 52 wrap the elastic members 51, and at the same time are at least fixed to the topsheet 10. In the present embodiment, the sheets 52 are configured by the elongation of the sidesheet 30.

Such a leakage-preventing unit 50 rises toward the wearer's side due to shrinkage of the elastic members 51 at the time of wearing, and forms a hollow shape (see FIG. 2).

Here, the aforementioned end unit regions S have joint processing units 53A in which a joint process for joining the portions where sheets 52 face each other is performed, and a non-joint processing unit 53B in which a joint process is not performed.

As shown in FIG. 3, a plurality of joint processing units 53A are provided at a predetermined interval on a plurality of first lines L1 along a predetermined direction, and at the same time, are provided at a predetermined interval on a plurality of second lines L2 along a direction perpendicular to a predetermined direction. That is, the first line L1 and the second line L2 form a cross, and the joint processing units 53A are provided at the intersection point of the first line L1 and the second line L2. Furthermore, the joint processing units 53A form a rectangular shape in the plan view of the absorbent article 1.

The direction (rectilinear) in which the first lines L1 extend is different from the direction in which the elastic members 51 expand and contract (that is, the longitudinal direction L of the absorbent article 1). The first line L1 is desired to be inclined at an angle less than 90 degrees (angle α of FIG. 3) with respect to a line along the direction in which the elastic members 51 expand and contract. Note that in the present embodiment, the first line L1 is inclined at 15 degrees with respect to the line along the direction in which the elastic members 51 expand and contract.

As shown in FIG. 3 (b), the width W1 of a joint processing unit 53A along the widthwise direction W of the absorbent article 1 is lesser than an interval S1 between two adjoining elastic members 51. Furthermore, the width W1 of the joint processing unit 53A is more than the width W2 of an elastic member 51 along the widthwise direction W of the absorbent article 1.

Figure 4:
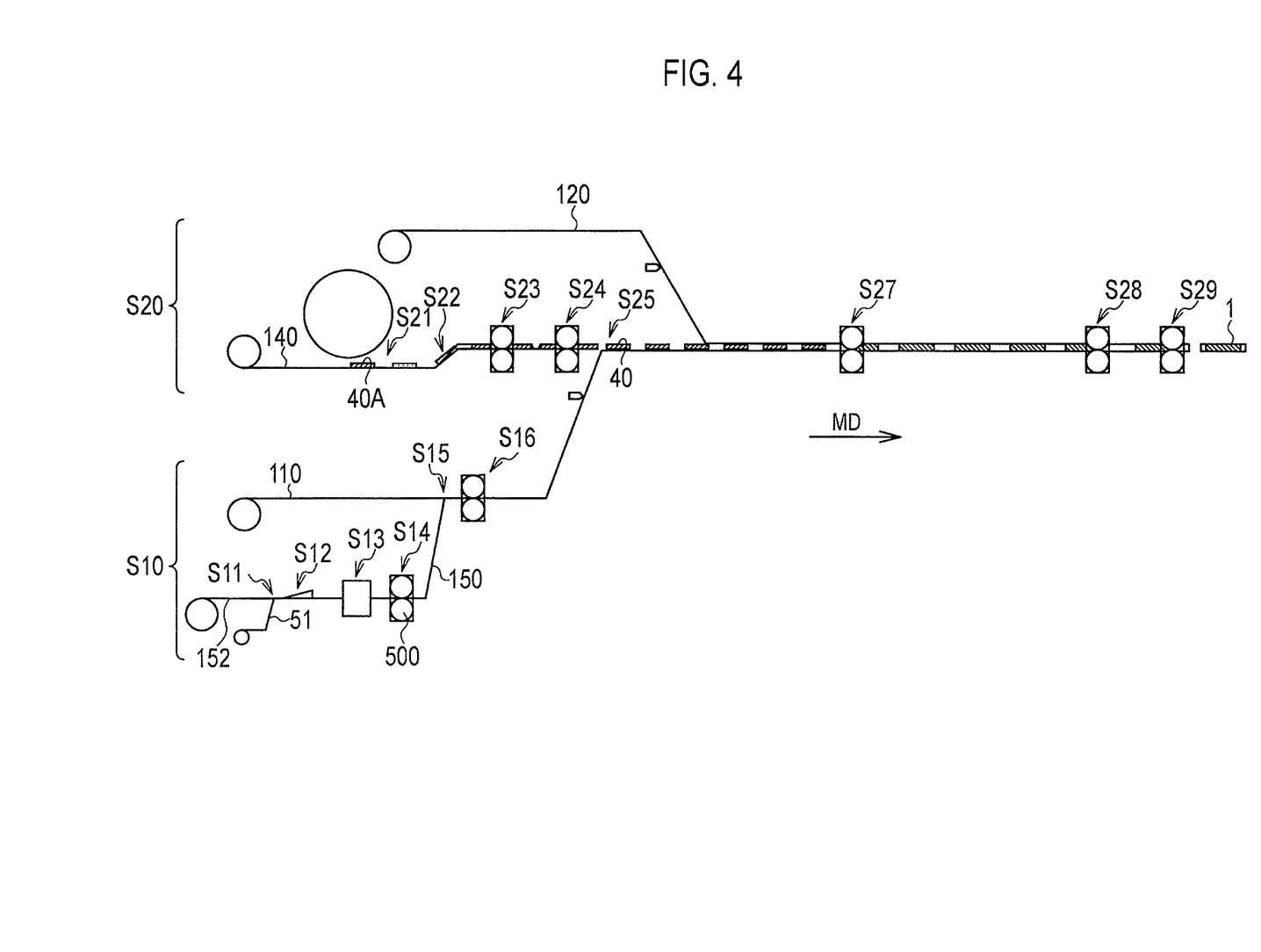
FIG. 4 is a diagram for explaining a method for manufacturing the absorbent article according to the present embodiment.

Next, a method for manufacturing an absorbent article according to the present embodiment is explained with reference to drawings. FIG. 4 is a diagram for explaining a method for manufacturing an absorbent article according to the present embodiment.

As shown in FIG. 4, the method for manufacturing the absorbent article includes a leakage-preventing unit forming line S10 and a main body line S20.

The leakage-preventing unit forming line S10 is configured by an elastic member joining step S11, a sheet-folding step S12, a leakage-preventing unit forming step S13, a sheet temporary joining step S14, a leakage-preventing unit pasting step S15, and a leakage-preventing unit fixing step S16.

In the an elastic member joining step S11, a plurality of elastic members 51 configuring the leakage-preventing unit 50 are joined with a pair of sheet continuous bodies 152 in which sheets 52 (sidesheets 30) configuring the leakage-preventing unit 50 are in continuation.

In the sheet-folding step S12, by folding both-side edges of the pair of sheet continuous bodies 152 with which a plurality of elastic members 51 are joined, each of the plurality of elastic members 51 is wrapped.

In the leakage-preventing unit forming step S13, by folding the sheet continuous bodies 152 that wrap the plurality of elastic members 51 in a predetermined shape, a leakage-preventing unit continuous body 150 in which the leakage-preventing units 50 are in continuation is formed.

In the sheet temporary joining step S14, the aforementioned joint processing unit 53A is formed at a position corresponding to the end unit regions S of the post-manufacturing leakage-preventing unit 50 in the leakage-preventing unit continuous body 150 by the joint processing device 500 described later.

In the leakage-preventing unit pasting step S15, the leakage-preventing unit continuous body 150 in which the joint processing unit 53A is formed is pasted to a topsheet continuous body 110 in which the topsheets 10 are in continuation.

In the leakage-preventing unit fixing step S16, the leakage-preventing unit continuous body 150 is fixed to the topsheet continuous body 110 by applying pressure (for example, performing embossing) to the topsheet continuous body 110 and the leakage-preventing unit continuous body 150 in the thickness direction T of the absorbent article 1.

The main body line S20 is configured by: an absorbent material laminating step S21; a covering material folding step S22; a covering material joining step S23; an absorber cutting step S24; an absorber laminating step S25; a backsheet pasting step S26; a joint unit forming step S27; an article outer shape joining step S28; and an article outer shape cutting step S29.

In the absorbent material laminating step S21, a mixed powder (not indicated in the figure) of ground pulp and high absorbent polymer is collected and the absorbent material 40A is molded, following which the molded absorbent material 40A is laminated at a predetermined interval on a covering-member continuous body 140 in which the covering materials 40B are in continuation.

In the covering material folding step S22, both-side edges of a crossing direction CD crossing a conveyance direction MD of the covering-member continuous body 140 are folded back on the absorbent material 40A.

In the covering material joining step S23, in order to correspond to the size of the absorber 40 of a single product, the absorber 40A and the covering-member continuous body 140 are joined by applying pressure (for example, performing embossing) to the covering-member continuous body 140 that covers the absorbent material 40A at a predetermined interval in the thickness direction T of the absorbent article 1.

In the absorber cutting step S24, the covering-member continuous body 140 that covers the absorbent material 40A at a predetermined interval is cut in accordance with the size of the absorber 40 of a single product, and the absorber 40 is formed.

In the absorber laminating step S25, an adhesive (for example, hot-melt) is applied to the topsheet continuous body 110 to which the leakage-preventing unit continuous body 150 is pasted, and then the absorber 40 is laminated at a predetermined interval to the topsheet continuous body 110.

In the backsheet pasting step S26, a backsheet continuous body 120 in which backsheets 20 on which the adhesive (for example, hot melt) has been applied are in continuation is pasted to the topsheet continuous body 110 on which the absorber 40 has been laminated. Thus, the absorber 40 is provided between the topsheet continuous body 110 and the backsheet continuous body 120.

In the joint unit forming step S27, the joint unit 80 in which at least the topsheet 10 and the absorber 40 are joined is formed by applying pressure (for example, performing embossing) at least to the topsheet continuous body 110 and the absorber 40 in the thickness direction T of the absorbent article 1.

In the article outer shape joining step S28, in order to correspond to the outer shape of the absorbent article 1, the topsheet continuous body 110 and the backsheet continuous body 120 are joined by applying pressure (for example, performing embossing) to the topsheet continuous body 110 and the backsheet continuous body 120 in the thickness direction T of the absorbent article 1.

In the article outer shape cutting step S29, in order to correspond to the outer shape of the absorbent article 1, the topsheet continuous body 110 and the backsheet continuous body 120, and the leakage-preventing unit 50, etc. are cut and the absorbent article 1 is manufactured.

Figure 5:
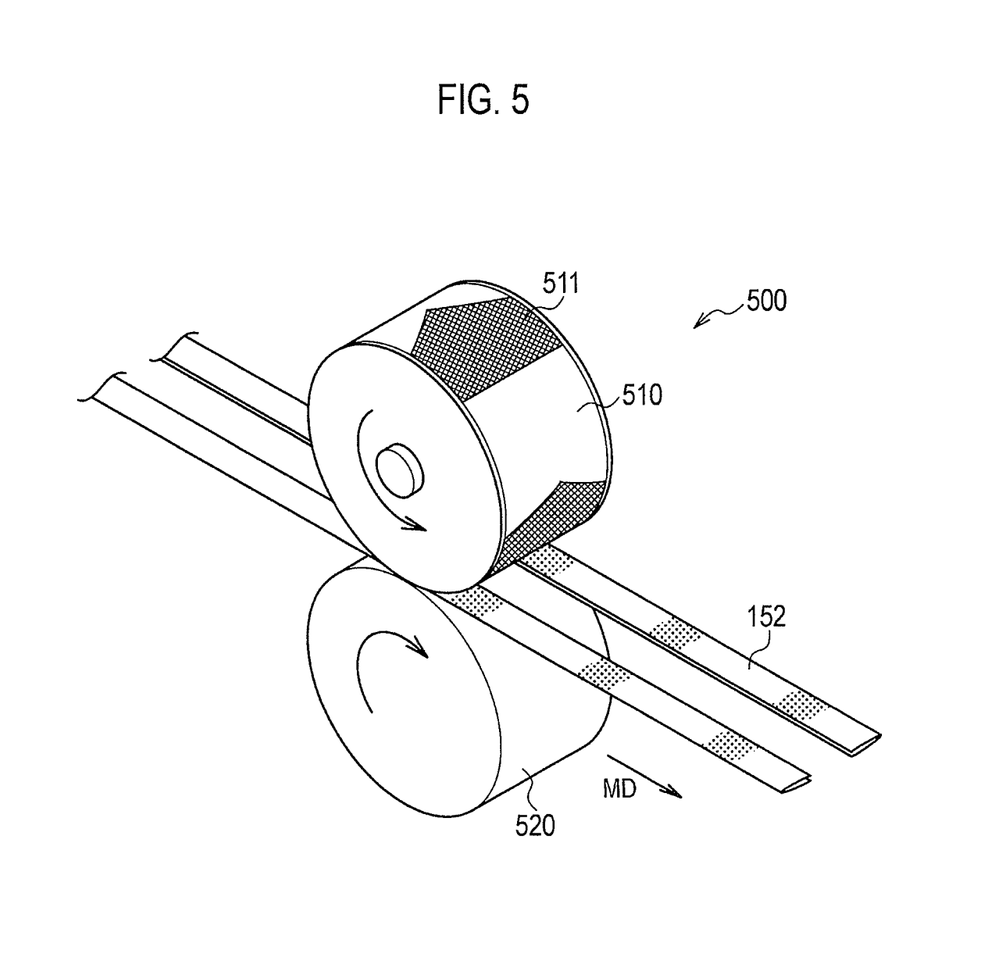
FIG. 5 is a perspective view showing a joint processing device 500 according to the present embodiment.
Figure 6:
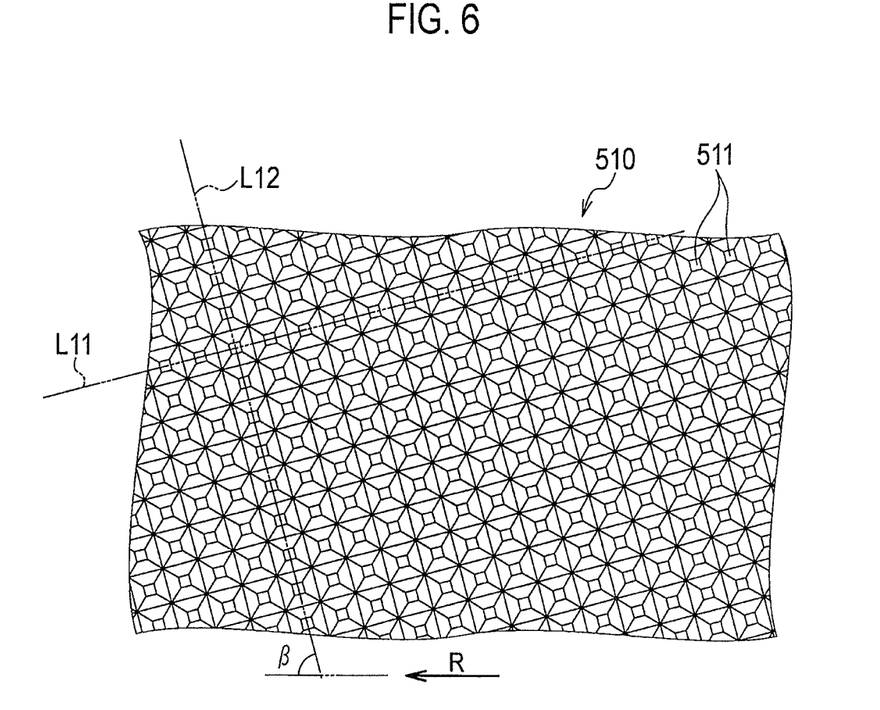
FIG. 6 is an exploded view showing an outer circumference of an upper roll 510 according to the present embodiment.

Next, the joint processing device 500 according to the present embodiment is explained with reference to drawings. FIG. 5 is a perspective view showing the joint processing device 500 according to the present embodiment. FIG. 6 is an exploded view showing an outer circumference of the upper roll 510 according to the present embodiment.

As shown in FIG. 5, in the aforementioned sheet temporary joining step S14, the joint processing device 500 forms cross-shaped joint processing units 53A at the position corresponding to the end unit regions S of the leakage-preventing unit 50 in the sheet continuous bodies 152 that wrap a plurality of elastic members 51. The joint processing device 500 includes an upper roll 510 and a lower roll 520.

A plurality of projections 511 are formed on an outer circumference of the upper roll 510. The plurality of projections 511 are in a rectangular shape as shown in FIG. 6. Specifically, a plurality of projections 511 are provided on the outer circumference of the upper roll 510 at a predetermined interval on a plurality of first lines L11 along a predetermined direction so as to correspond to the first line L1 of the joint processing unit 53A. Furthermore, a plurality of projections 511 are provided on the outer circumference of the upper roll 510 at a predetermined interval on a plurality of second lines L12 along a direction perpendicular to a predetermined direction so as to correspond to the second line L2 of the joint processing unit 53A. That is, the first line L11 and the second line L12 form a cross, and the plurality of projections 511 are provided at the intersection point of the first line L11 and the second line L12.

The direction in which the first line L11 extends is different from a roll rotation direction R (that is, a conveyance direction MD of the sheet continuous body 152). The first line L11 is desired to be inclined at an angle less than 90 degrees (angle δ of FIG. 6) with respect to a line along the roll rotation direction R.

The lower roll 520 faces the upper roll 510 on both sides of the sheet continuous body 152. A plurality of projections are not formed on an outer circumference of the lower roll 520. Note that a plurality of projections may be formed facing the plurality of projections 511 on the outer circumference of the lower roll 520.

In the aforementioned embodiment, the fixed units 51A of the elastic member 51 are provided in at least the boundary of the central region C and the end unit regions S. Thus, the elastic members 51 shrink the boundary portion positioned on the inner side from the outer end of the longitudinal direction L of the absorbent article 1 in a direction in which they come closer to each other. Therefore, as compared to the conventional absorbent article in which the elastic members 51 are fixed in the sheet 52 at the outer ends of the longitudinal direction L of the absorbent article 1, the falling down of the end unit regions S (that is, the outer ends of the longitudinal direction L of the absorbent article 1) in the central region C (absorbing surface) side by more than what is needed, at the time of wearing, can be prevented. Therefore, the form of the absorbent article 1 is stable at the time of wearing, and the wearer can wear the absorbent article 1 assuredly.

Furthermore, the absorbent article 1 is formed in a continuous state in the longitudinal direction L of the absorbent article 1 (a so-called vertical flow method). Thus, as described above, the fixed unit 51A of the elastic member 51 is provided in at least the boundary of the central region C and the end unit regions S. The fixed unit 51A of the elastic member 51 is joined with the sheet continuous body 152 in an extended state in the conveyance direction MD of the sheet continuous body 152. Therefore, when the leakage-preventing unit 50 is cut in the article outer shape cutting step S29, the elastic member 51 is in an extended state between the fixed units 51A, and the outer side (that is, the end unit regions S) of the longitudinal direction L of the absorbent article 1 from the fixed unit 51A is the free end 51B. Because the free end 51B is controlled by the joint processing unit 53A during shrinkage along the longitudinal direction L of the absorbent article 1 at the time of cutting, the meandering and buckling of the free end 51B can be prevented. Thus, the deterioration in the appearance of the absorbent article 1 can be prevented.

Note that because the leakage-preventing units 50 rise toward the wearer due to shrinkage of the elastic members 51, at the time of wearing, between the fixed units 51A, that is, in the central region C, the leakage of the bodily waste of the wearer from the absorbent article 1 can be prevented.

The end unit regions S can be joined as one part in the absorber 40 having strength more than the leakage-preventing unit 50, and the form of the absorbent article 1 can be stabilized. However, because the area in which the absorber 40 and the end unit regions S are joined needs to be increased, the flexibility of the end unit regions S in which the joint process is executed is lost.

By contrast, in the present embodiment, a joint processing unit 53A and a non-joint processing unit 53B are provided, and therefore, as compared to the case where the end unit regions S are joined as one part with the absorber 40, the area in which the portions where the sheets 52 face each other in the end unit regions S (that is, the area of the joint processing unit 53A) are joined can be reduced. Therefore, it is difficult for the end unit regions S to harden, and the flexibility of the end unit regions S can be maintained. Thus, it becomes difficult for the wearer to feel discomfort at the time of wearing, and it is possible to inhibit the wearer's comfortable feel against the skin from worsening.

In the present embodiment, a plurality of joint processing units 53A are provided at a predetermined interval on the first line L1, and at the same time, are provided at a predetermined interval on the second line L2. Thus, as compared to the case where the joint processing units 53A are formed along the first line L1 and the second line L2, the area in which the portions where the sheets 52 face each other in the end unit regions S are joined can be reduced further. Therefore, it is further difficult for the end unit regions S to harden, and the flexibility of the end unit regions S can be improved.

Furthermore, the free ends 51B of the elastic members 51 shrink between the plurality of joint processing units 53A provided at a predetermined interval. Thus, the free ends 51B are controlled by the joint processing unit 53A in the end unit regions S, and therefore, they shrink along the longitudinal direction L of the absorbent article 1. Because the meandering and buckling of the free end 51B can certainly be prevented, the deterioration in the appearance of the absorbent article 1 can be prevented.

In the present embodiment, the width W1 of the joint processing unit 53A along the widthwise direction W of the absorbent article 1 is lesser than the interval S1 between two adjoining elastic members 51. Thus, as compared to the case where the width W1 of the joint processing unit 53A is more than the interval S1 of the elastic members 51, the area in which the portions where the sheets 52 face each other in the end unit regions S (that is, the area of the joint processing unit 53A) are joined can be reduced further.

In the present embodiment, the direction in which the first line L1 extends is different from the direction in which the elastic members 51 expand and contract (that is, the longitudinal direction L of the absorbent article 1). For example, in cases where the direction in which the first line L1 extends is the same as the direction in which the elastic members 51 expand and contract, if the joint processing units 53A and the elastic members 51 overlap, the overlapping portion will be arranged continuously in the longitudinal direction L of the absorbent article 1. In such cases, the portions where the sheets 52 face each other in the end unit regions S are joined in certain parts. That is, it may not be possible to control the elastic members 51 by the joint processing units 53A. Therefore, the free ends 51B may meander and buckle during shrinkage resulting in deterioration in the appearance of the absorbent article 1. By contrast, if the direction in which the first line L1 extends is different from the direction in which the elastic members 51 expand and contract, the increase in the portions where the joint processing units 53A and the elastic members 51 overlap by more than what is required can be prevented. Thus, the elastic members 51 can certainly be controlled by the joint processing units 53A along the longitudinal direction L of the absorbent article 1, and the meandering and buckling of the free ends 51B can be prevented. Therefore, the deterioration in the appearance of the absorbent article 1 can be prevented.

In the present embodiment, the first line L1 is inclined at less than 90 degrees (15 degrees in the present embodiment) with respect to the line along the direction in which the elastic members 51 expand and contract. Note that if the first line L1 does not incline along the direction in which the elastic members 51 expand and contract, then when the joint processing units 53A and the elastic members 51 overlap, that is, when the first line L1 overlaps along the free end 51B, the free end 51B becomes fixed to the sheet 52, and due to shrinkage of the elastic members 51 fixed to the sheet 52 in the end unit regions S, the end unit regions S would fall easily in the central region C (absorbing surface) side, and the form of the absorbent article might be deformed at the time of wearing.

MODIFICATIONS

The joint processing units 53A of the leakage-preventing unit 50 according to the aforementioned embodiment can be modified as follows. Note that the same symbols have been used for the same portions as the leakage-preventing unit 50 according to the aforementioned embodiment, and mainly, the differences will be explained.

First Modification

Figure 7:
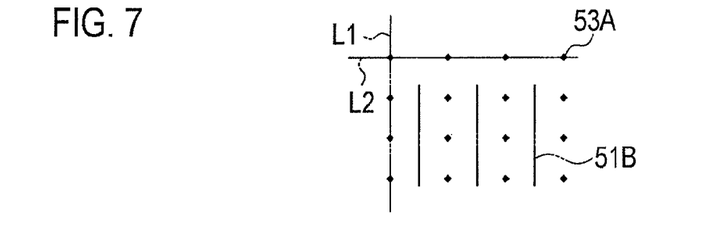
FIG. 7 is an enlarged plan view showing a part of a leakage-preventing unit 50A according to a first modification.

First of all, a leakage-preventing unit 50A according to a first modification is explained with reference to drawings. FIG. 7 is an enlarged plan view showing a part of the leakage-preventing unit 50A according to the first modification.

In the aforementioned embodiment, the direction in which the first line L1 extends in the joint processing units 53A of the leakage-preventing unit 50 is different from the direction in which the elastic members 51 expand and contract (that is, the longitudinal direction L of the absorbent article 1). By contrast, in the modification, as shown in FIG. 7, the direction in which the first line L1 extends in the joint processing units 53A of the leakage-preventing unit 50A is same as the direction in which the elastic members 51 expand and contract (that is, the longitudinal direction L of the absorbent article 1).

Figure 8:
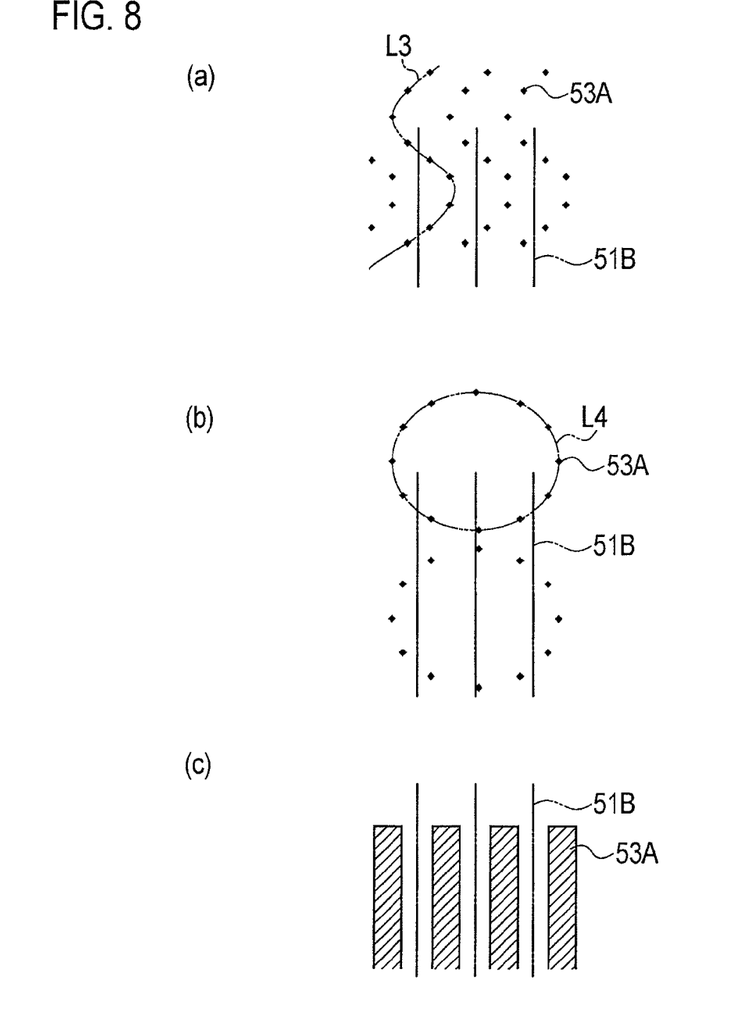
FIG. 8(a) is an example of joint processing unit of a leakage-preventing unit provided on a curved line.
FIG. 8(b) is an example of joint processing unit provided on a circular line.
FIG. 8(c) is an example of joint processing unit provided in all parts except the portions where elastic members and sheets come into contact.

Here, the joint processing units 53A need not necessarily be provided linearly (cross-wise), for example, as shown in FIG. 8 (*a*), they may be provided on a curved line L3, and as shown in FIG. 8 (*b*), they may be provided on a circular line L4.

Furthermore, as shown in FIG. 8 (*c*), the joint processing units 53A may be provided in all parts except the portions where the elastic members 51 and the sheets 52 come in contact. In such a case, the joint processing units 53A may be formed by performing the joint process in all parts except the portions where the elastic members 51 and the sheets 52 come in contact, or may be formed by performing the joint process in almost the entire end unit region S.

Second Modification

Figure 9:
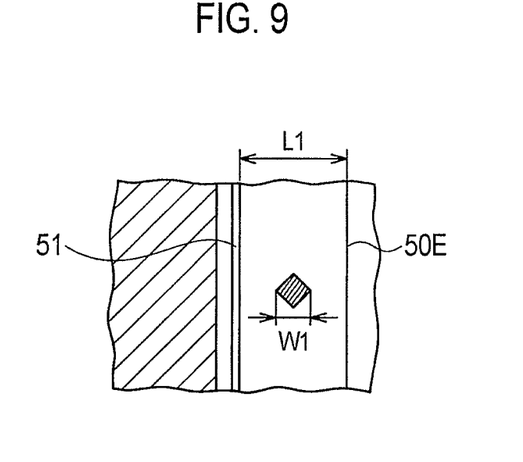
FIG. 9 is an enlarged plan view showing a part of a leakage-preventing unit 50B according to a second modification.

Next, a leakage-preventing unit 50B according to a second modification is explained with reference to drawings.

FIG. 9 is an enlarged plan view showing a part of the leakage-preventing unit 50B according to the second modification.

In the aforementioned embodiment, a plurality (five in the present embodiment) of elastic members 51 of the leakage-preventing unit 50 are provided at a predetermined interval in the widthwise direction W of the absorbent article 1. By contrast, in the second modification, as shown in FIG. 9, one elastic member 51 of the leakage-preventing unit 50B is provided.

In such a case, the width W1 of the joint processing unit 53A along the widthwise direction W of the absorbent article 1 is lesser than the distance L1 from the elastic member 51 up to the edge unit 50E of the leakage-preventing unit 50 in the widthwise direction W of the absorbent article 1.

Third Modification

Figure 10:
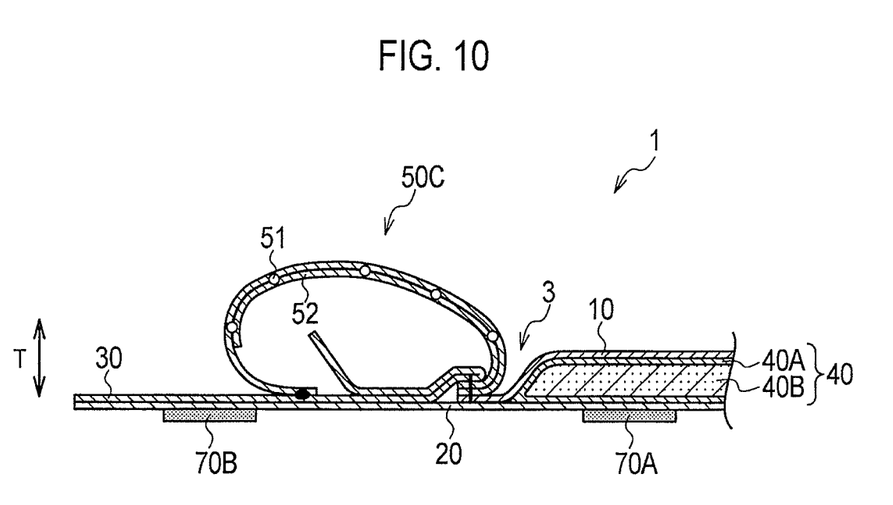
FIG. 10 is a cross-sectional view (part 1) of a part of a leakage-preventing unit 50C according to a third modification.

Next, a leakage-preventing unit 50C according to a third modification is explained with reference to drawings. FIG. 10 is a cross-sectional view of a part of a leakage-preventing unit 50C according to the third modification.

In the aforementioned embodiment, a sheet 52 of the leakage-preventing unit 50 is configured by the elongation of the sidesheet 30. By contrast, in the third modification, as shown in FIG. 10, the sheet 52 of the leakage-preventing unit 50C is configured by a sheet separate from the topsheet 10 and the sidesheet 30. The leakage-preventing unit 50C rises toward the wearer's side due to shrinkage of the elastic members 51 at the time of wearing, and forms a hollow shape.

Figure 11:
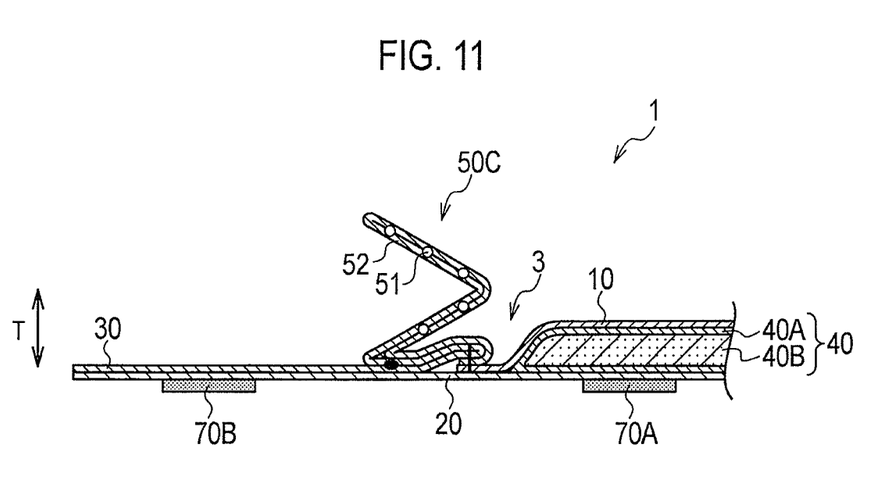
FIG. 11 is a cross-sectional view (part 2) of a part of a leakage-preventing unit 50C according to the third modification.
Figure 12:
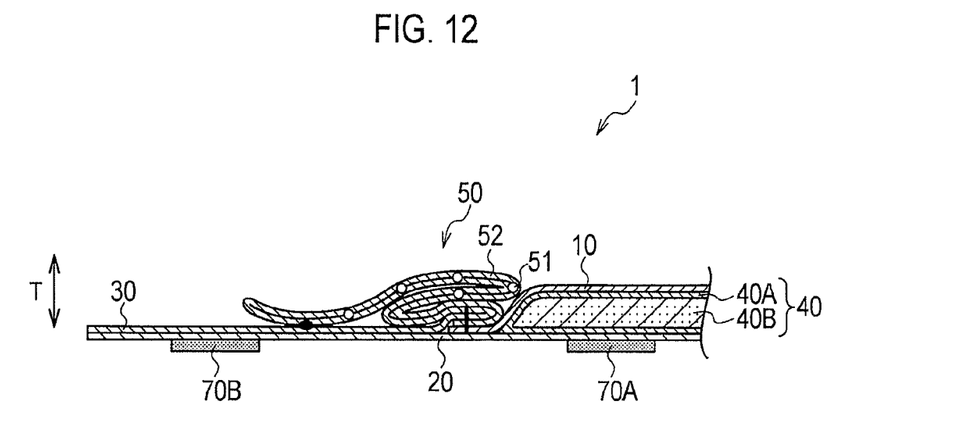
FIG. 12 is a cross-sectional view (part 3) of a part of a leakage-preventing unit 50C according to the third modification.
Figure 13:
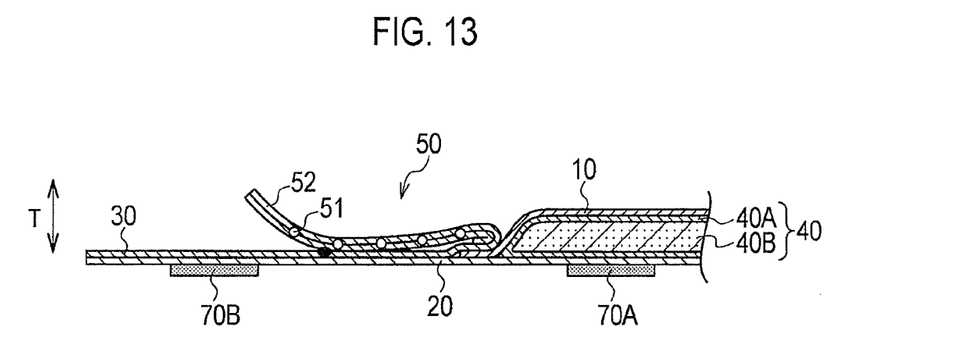
FIG. 13 is a cross-sectional view (part 4) of a part of a leakage-preventing unit 50C according to the third modification.

Here, the leakage-preventing unit 50C need not necessarily form a hollow shape, for example, as shown in FIG. 11 and FIG. 12, a plurality of leakage-preventing units may be folded on both side units 3 of the absorbent article 1, and as shown in FIG. 13, the leakage-preventing unit may be folded once on both side units 3 of the absorbent article 1. That is, there is no particular limitation as far as the configuration of the leakage-preventing unit 50C is concerned, and any configuration may be adopted as long as the leakage-preventing unit 50C adheres to the wearer at the time of wearing.

Other Embodiments

As described above, the content of the present invention is disclosed through the embodiment. However, it should not be interpreted that the statements and drawings constituting a part of the present disclosure limit the present invention. From the present disclosure, various alternative embodiments, examples, and operational technologies will become apparent to those skilled in the art.

For example, the embodiment can be changed as follows: Specifically, the explanation is based on the fact that the absorbent article 1 is a sanitary napkin, but the present invention is not limited thereto, and as long as a leakage-preventing unit is provided, for example, even a disposable diaper may be applicable.

Furthermore, the configuration of the absorbent article 1 is not particularly limited, and, it is of course that it can be set according to the purpose.

Furthermore, it is explained that the elastic members 51 are fixed to the sheet 52 with the fixed unit 51A being in at least the boundary of the central region C and the end unit regions S, but the present invention is not limited thereto, and the elastic members 51 may be fixed to the sheet 52 in the entire central region C.

Furthermore, it is explained that the joint processing units 53A form a rectangular shape in the plan view of the absorbent article 1, but the present invention is not limited thereto, for example, they may form a circular shape or a polygonal shape (such as a triangular shape and a pentagonal shape).

As described above, it is of course that the present embodiment includes various embodiments and the like not described here. Therefore, the technical scope of the embodiments is defined only by the technical characteristics according to claims appropriate from the above-described explanations.

According to the embodiments, when a leakage-preventing unit is provided, an absorbent article capable of inhibiting the wearer's comfortable feel against the skin from worsening while stabilizing the shape of the absorbent article can be provided.

The invention claimed is:

1. An absorbent article comprising a topsheet having liquid permeability, a backsheet having liquid impermeability, an absorber provided between the topsheet and the backsheet, and a pair of leakage-preventing units provided on both longitudinal sides of the absorbent article with, a leakage-preventing unit comprising elastic members arranged along the longitudinal direction of the absorbent article, and sheets arranged along the longitudinal direction, which wrap the elastic members and have at least a part fixed to the topsheet, wherein the leakage-preventing unit comprises:
a central region in the longitudinal direction; and
a pair of end unit regions positioned outside the central region in the longitudinal direction, the elastic members comprise:
a fixed unit fixed to the sheets so that the elastic members extend in the longitudinal direction in at least the boundary between the central region and the end unit regions; and
free ends positioned outside the fixed unit in the longitudinal direction, the free ends not being fixed to the sheets, the end unit regions comprise:
a plurality of joint processing units in each of which a joint process for joining the portions where the sheets face each other is performed; and
a non-joint processing unit in which the joint process is not performed, and the free ends are arranged in the non-joint processing unit so that the free ends are disposed between the joint processing units in a width direction of the absorbent article, and wherein the plurality of joint processing units are provided at a predetermined interval on a plurality of first lines along a predetermined direction, and at the same time, are provided at a predetermined interval on a plurality of second lines along a direction perpendicular to the predetermined direction, the first lines and the second lines intersect each other, and the joint processing units are provided at intersections of the first line and the second lines.

2. The absorbent article according to claim 1, wherein a plurality of elastic members are provided at a predetermined interval in the widthwise direction of the absorbent article, and the width of a joint processing unit along the widthwise direction is lesser than an interval between two adjoining elastic members.

3. The absorbent article according to claim 1 or 2, wherein the direction in which the first line extends is different from the direction in which the elastic members expand and contract.

4. The absorbent article according to claim 3, wherein the first line inclines at an angle less than 90 degrees with respect to a line along a direction in which the elastic members expand and contract.

* * * * *